United States Patent
Ajito et al.

(10) Patent No.: US 11,911,150 B2
(45) Date of Patent: Feb. 27, 2024

(54) COMPONENT CONCENTRATION MEASUREMENT DEVICE

(71) Applicant: Nippon Telegraph and Telephone Corporation, Tokyo (JP)

(72) Inventors: Katsuhiro Ajito, Tokyo (JP); Michiko Seyama, Tokyo (JP); Daichi Matsunaga, Tokyo (JP); Masahito Nakamura, Tokyo (JP); Yujiro Tanaka, Tokyo (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 734 days.

(21) Appl. No.: 17/047,609

(22) PCT Filed: Apr. 5, 2019

(86) PCT No.: PCT/JP2019/015141
§ 371 (c)(1),
(2) Date: Oct. 14, 2020

(87) PCT Pub. No.: WO2019/203029
PCT Pub. Date: Oct. 24, 2019

(65) Prior Publication Data
US 2021/0121105 A1    Apr. 29, 2021

(30) Foreign Application Priority Data
Apr. 16, 2018   (JP) ................. 2018-078215

(51) Int. Cl.
*A61B 5/145*    (2006.01)
*A61B 5/00*     (2006.01)

(52) U.S. Cl.
CPC ........ *A61B 5/14532* (2013.01); *A61B 5/0095* (2013.01)

(58) Field of Classification Search
CPC .............. A61B 5/1455; A61B 5/14551; A61B 5/14532; A61B 5/0095
See application file for complete search history.

(56) References Cited

U.S. PATENT DOCUMENTS

| | | | |
|---|---|---|---|
| 2007/0197886 A1 | 8/2007 | Naganuma et al. | |
| 2013/0044563 A1* | 2/2013 | Watanabe | A61B 5/0095 367/7 |
| 2014/0066743 A1 | 3/2014 | Nakajima et al. | |

(Continued)

FOREIGN PATENT DOCUMENTS

| | | |
|---|---|---|
| CN | 203988073 U | 12/2014 |
| JP | 2010104858 A | 5/2010 |
| JP | 2014066701 A | 4/2014 |

*Primary Examiner* — Chu Chuan Liu
(74) *Attorney, Agent, or Firm* — Slater Matsil, LLP

(57) ABSTRACT

A light irradiation unit configured to irradiate a measurement part with a light beam that has a wavelength absorbed by glucose and a detection unit configured to detect a photoacoustic signal generated from the measurement part irradiated with the light beam emitted from the light irradiation unit are included. The light irradiation unit irradiates the measurement part by scanning the light beam 2-dimensionally. The measurement part is irradiated with the light beam through raster scanning. For example, the light beam has a beam diameter of about 100 μm and is scanned at a scanning speed of about 100 μm/10 ms.

14 Claims, 5 Drawing Sheets

(56) References Cited

U.S. PATENT DOCUMENTS

2014/0118749 A1\* 5/2014 Nakajima .............. G01H 9/002
  356/519
2014/0206960 A1\* 7/2014 Nagae .................... A61B 5/145
  600/407

\* cited by examiner

# COMPONENT CONCENTRATION MEASUREMENT DEVICE

CROSS-REFERENCE TO RELATED APPLICATIONS

This application is a national phase entry of PCT Application No. PCT/JP2019/015141, filed on Apr. 5, 2019, which claims priority to Japanese Application No. 2018-078215, filed on Apr. 16, 2018, which applications are hereby incorporated herein by reference.

TECHNICAL FIELD

The present invention relates to a constituent concentration measurement device that measures a concentration of glucose in a non-invasive manner.

BACKGROUND

It is important to determine a dosage of insulin for a diabetic and ascertain (measure) a blood-sugar level from the viewpoint of prevention or the like of diabetes. A blood-sugar level is a concentration of glucose in blood and a photoacoustic method is well known as a method of measuring such a kind of component concentration (see PTL 1).

When a living body is irradiated with a certain amount of light (an electromagnetic wave), the radiated light is absorbed by molecules contained in the living body. Therefore, measurement target molecules in the part irradiated with the light are locally heated, expand, and thus produce sound waves. A pressure of the sound waves depends on the number of molecules absorbing the light. A photoacoustic method is a method of measuring the number of molecules inside a living body by measuring the sound waves. Sound waves are pressure waves that propagate in a living body and have a feature in which diffusion is more difficult than electromagnetic waves. Thus, the photoacoustic method can be appropriate for measuring blood components of a living body.

In measurement according to the photoacoustic method, it is possible to monitor the concentration of glucose in blood continuously. In the measurement of the photoacoustic method, a blood sample is not necessary and a measurement subject may not feel discomfort.

CITATION LIST

Patent Literature

PTL 1—Japanese Patent Application Publication No. 2010-104858.

SUMMARY

Technical Problem

However, in measurement of glucose in a human body according to a photoacoustic method, a measurement part is irradiated with light. Therefore, a temperature of tissues of the skin or the like of a part irradiated with the light as well as molecules of a measurement target may increase. Therefore, in the case of continuous measurement, there is a problem that a temperature serving as a standard for a spot (surrounding tissues) in which there is a measurement target glucose increases and measurement precision deteriorates.

Embodiments of the present invention have been devised to solve the foregoing problem and an objective of the present invention is to curb deterioration in measurement precision due to an increase in a temperature at the time of measurement of glucose in a human body according to a photoacoustic method.

Means for Solving the Problem

According to an aspect of the present invention, a component concentration measurement device includes: a light irradiation unit configured to irradiate a measurement part with a light beam that has a wavelength absorbed by glucose; and a detection unit configured to detect a photoacoustic signal generated from the measurement part irradiated with the light beam emitted from the light irradiation unit. The light irradiation unit irradiates the measurement part by scanning the light beam 2-dimensionally.

In the component concentration measurement device, the light irradiation unit may irradiate the measurement part by performing raster scanning with the light beam.

In the component concentration measurement device, the light irradiation unit may scan the light beam within a detection range of the detection unit and irradiate the measurement part.

In the component concentration measurement device, the light irradiation unit may intermittently scan the light beam at a set time interval.

In the component concentration measurement device, the light irradiation unit may include a light source unit configured to generate the light beam that has a wavelength absorbed by glucose, and a scanning unit configured to scan the light beam generated by the light source unit.

The component concentration measurement device may further include a beam shaping unit configured to extract a central portion of the light beam generated by the light source unit.

Effects of Embodiments of the Invention

As described above, according to embodiments of the present invention, the light irradiation unit irradiates a measurement part by scanning a light beam 2-dimensionally. Therefore, it is possible to obtain the excellent advantageous effect of suppressing deterioration in measurement precision due to an increase in a temperature at the time of measurement of glucose in a human body according to a photoacoustic method.

DETAILED DESCRIPTION OF ILLUSTRATIVE EMBODIMENTS

Figure 1:
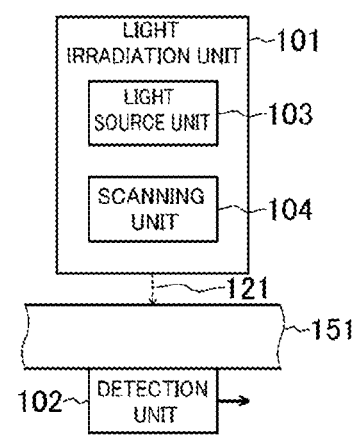
FIG. 1 is a diagram illustrating a configuration of a component concentration measurement device according to an embodiment of the present invention.

Hereinafter, a component concentration measurement device according to an embodiment of the present invention will be described with reference to FIG. 1. The component concentration measurement device includes a light irradiation unit 101 that irradiates a measurement part 151 with the light beam 121 with a wavelength absorbed by glucose and a detection unit 102 that detects a photoacoustic signal generated from the measurement part 151 irradiated with the light beam 121 emitted from the light irradiation unit 101.

Figure 2:
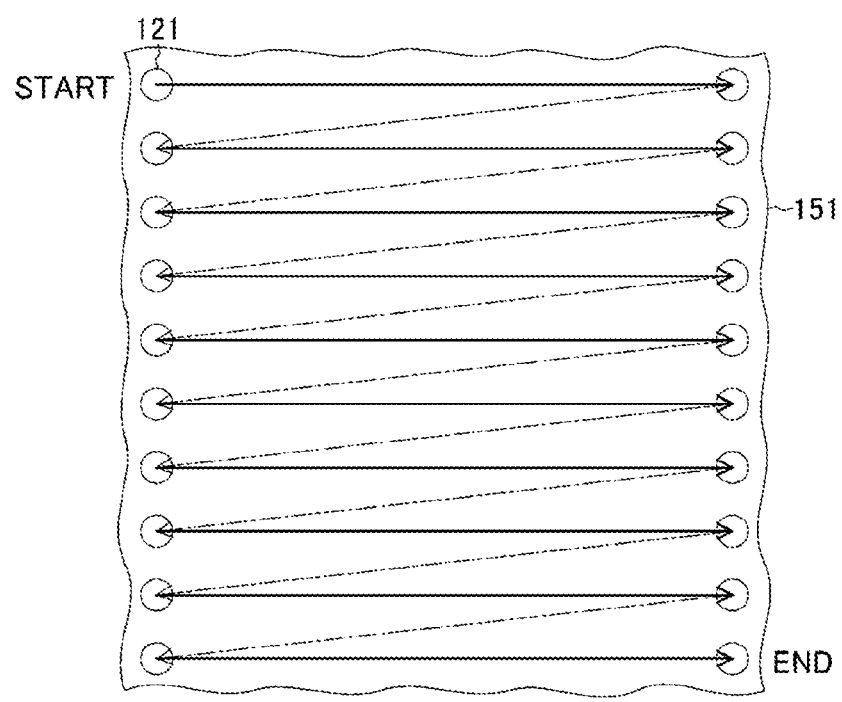
FIG. 2 is a plan view illustrating a scanning state of a light beam 121.

Here, in embodiments of the present invention, the light irradiation unit 101 irradiates the measurement part 151 by scanning the light beam 121 2-dimensionally. For example, as illustrated in FIG. 2, the measurement part 151 is irradiated with the light beam 121 through raster scanning. For example, the light beam 121 has a beam diameter of about 100 μm. The scanning is performed at a scanning speed of about 100 μm/10 ms. For example, the light irradiation unit 101 irradiates the measurement part 151 by scanning the light beam 121 within a detection range of the detection unit 102. For example, a square area with a side of 1 mm is scanned. The measurement part 151 is, for example, a part of a human body such as a finger or an earlobe.

For example, the light irradiation unit 101 includes a light source unit 103 that generates light beam with a wavelength absorbed by glucose and a scanning unit 104 that scans the light beam generated by the light source. The scanning unit 104 scans the above-described light beam 121. For example, the scanning unit 104 scans the light beam 121 by a galvano-mirror. For example, the scanning unit 104 scans the light beam 121 by using a well-known MEMS mirror.

Since the light beam 121 is radiated in this way, it is possible to curb an increase in a temperature of tissues. As well known, an increase in a temperature of tissues is later than generation of sound waves by thermal expansion of a measurement target caused at the time of radiation of the light beam 121. Accordingly, when the light beam 121 is moved to another spot before an increase in a temperature of tissues such as the skin by scanning the light beam 121, it is possible to curb an increase in a temperature of surrounding tissues in which there is a measurement target glucose. As a result, according to the embodiment, it is possible to curb deterioration of measurement precision due to an increase in a temperature at the time of measurement of glucose in a human body according to a photoacoustic method.

Figure 3:
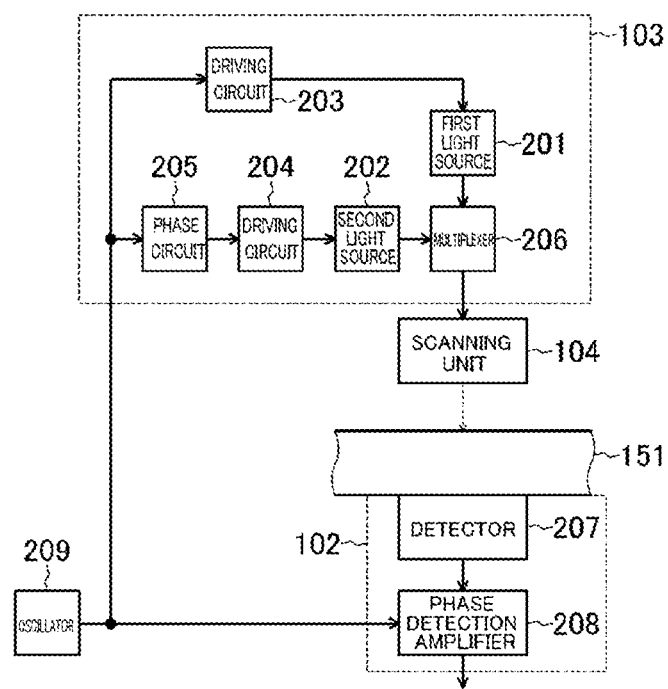
FIG. 3 is a diagram illustrating a further detailed configuration of a component concentration measurement device according to an embodiment of the present invention.

Here, the component concentration measurement device will be described in more detail with reference to FIG. 3. The component concentration measurement device includes a first light source 201, a second light source 202, a driving circuit 203, a driving circuit 204, a phase circuit 205, a multiplexer 206, a detector 207, a phase detection amplifier 208, and an oscillator 209. The first light source 201, the second light source 202, the driving circuit 203, the driving circuit 204, the phase circuit 205, and the multiplexer 206 are included in the light source unit 103. The detector 207 and the phase detection amplifier 208 are included in the detection unit 102.

The oscillator 209 is connected to each of the driving circuit 203, the phase circuit 205, and the phase detection amplifier 208 via signal lines. The oscillator 209 transmits a signal to each of the driving circuit 203, the phase circuit 205, and the phase detection amplifier 208.

The driving circuit 203 receives a signal transmitted from the oscillator 209, supplies driving power to the first light source 201 connected via the signal line, and oscillates the first light source 201. The first light source 201 is, for example, a semiconductor laser.
The phase circuit 205 receives a signal transmitted from the oscillator 209 and transmits s signal obtained by changing a phase of the received signal by 180° to the driving circuit 204 connected via the signal line.

The driving circuit 204 receives the signal transmitted from the phase circuit 205, supplies driving power to the second light source 202 connected via a signal line, and oscillates the second light source 202. The second light source 202 is, for example, a semiconductor laser.

The first light source 201 and the second light source 202 output light with mutually different wavelengths and the light output by each light source is guided to the multiplexer 206 by a light wave transmitter. A wavelength of one of the light of the first light source 201 and the light of the second light source 202 is set to a wavelength absorbed by glucose and a wavelength of the other light is set to a wavelength absorbed by water. The wavelengths are set so that the degree of absorption of glucose and water is equal.

The light output from the first light source 201 and the light output from the second light source 202 are combined by the multiplexer 206 to be incident as a light beam on the scanning unit 104. The scanning unit 104 on which the light beam is incident scans the incident light beam and the measurement part 151 is irradiated with the light beam. The measurement part 151 to which the light beam is scanned and radiated in this way generates a photoacoustic signal therein.

The detector 207 detects the photoacoustic signal generated in the measurement part 151, converts the photoacoustic signal into an electric signal, and transmits the electric signal to the phase detection amplifier 208 connected via a signal line. The phase detection amplifier 208 receives a synchronous signal necessary to detect a synchronous wave transmitted from the oscillator 209, receives an electric signal proportional to the photoacoustic signal transmitted from the detector 207, performs synchronization wave detection, amplification, and filtering, and outputs the electric signal proportional to the photoacoustic signal.

The first light source 201 outputs light with modulated intensity in synchronization with an oscillating frequency of the oscillator 209. On the other hand, the second light source 202 outputs light with modulated intensity at the oscillating frequency of the oscillator 209 and in synchronization with the signal of which the phase is changed by 180° by the phase circuit 205.

Here, for the intensity of the signal output from the phase detection amplifier 208, the light output by each of the first light source 201 and the second light source 202 is proportional to an amount of light absorbed by components (glucose and water) inside the measurement part 151. Therefore, the intensity of the signal is proportional to the number of components inside the measurement part 151. A component concentration derivation unit (not illustrated) obtains the number of components of a measurement target (glucose) in the blood inside the measurement part 151 from a measurement value of the intensity of the signal output in this way.

In this way, since the intensity of the light output from the first light source 201 and the intensity of the light output from the second light source 202 are modulated in accordance with signals with the same frequency, there is no influence of non-uniformity of frequency characteristics of a measurement system which is problematic when the intensity is modulated in accordance with signals with a plurality of frequencies.

On the other hand, nonlinear absorption coefficient dependency which exists in a measurement value of a photoacoustic signal which is problematic in measurement according to a photoacoustic method can be solved through measurement using light with a plurality of wavelengths providing an equal absorption coefficient, as described above (see PTL 1).

Figure 4:
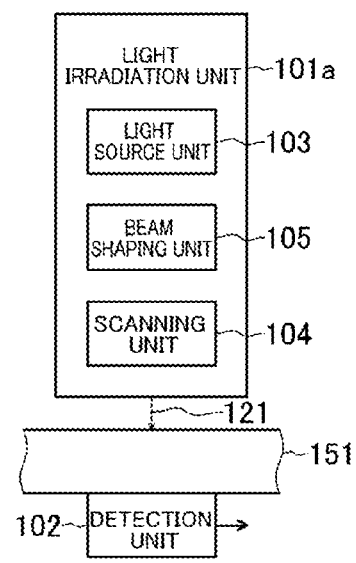
FIG. 4 is a diagram illustrating a configuration of another component concentration measurement device according to an embodiment of the present invention.

Incidentally, as illustrated in FIG. 4, a beam shaping unit 105 that extracts a central portion of the light beam generated by the light source unit 103 may be included to realize a light irradiation unit 101a. The light beam shaped by the beam shaping unit 105 is scanned by the scanning unit 104.

As well known, in the light beam formed by laser light, light intensity in a cross section has a normal distribution, and thus the light intensity of the central portion is high. In the case of the light beam, the beam is shaped, for example, by causing the light beam to pass through a pinhole and a beam diameter is broadened to, for example, about 100 μm. Thus, the light intensity in a cross-sectional direction of the light beam becomes uniform and light intensity per unit area decreases. Thus, it is possible to further curb an increase of a temperature of local tissues irradiated with the light beam.

Figure 5:
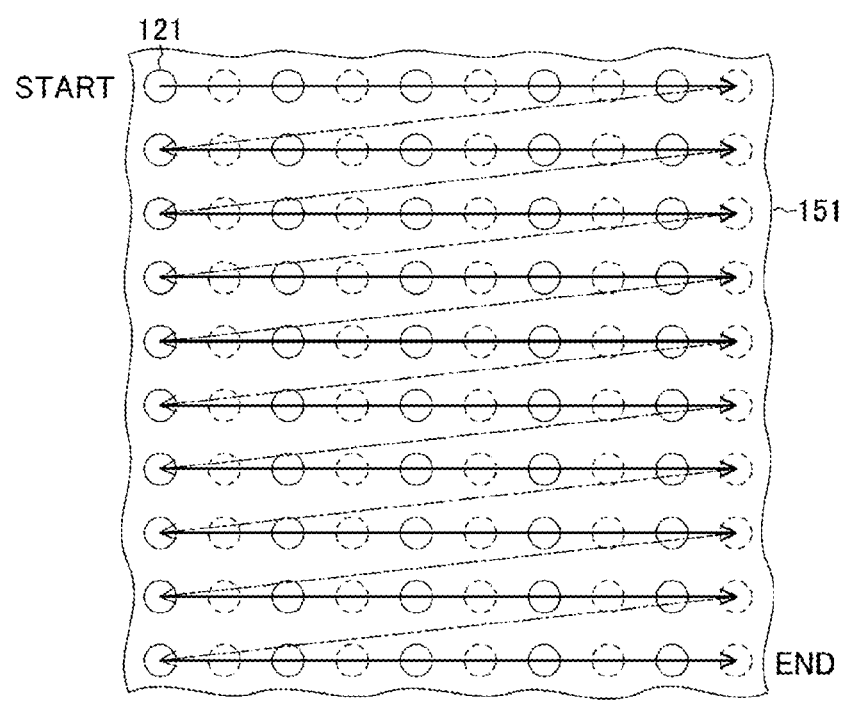
FIG. 5 is a plan view illustrating a scanning state of the light beam 121.

As illustrated in FIG. 5, the measurement part may be intermittently irradiated with the scanned light beam 121. For example, the light beam is scanned at about 100 μm/10 ms and the irradiation of the light beam 121 is turned on or off at intervals of 10 ms. Thus, it is possible to further curb an increase in a temperature of surrounding tissues.

As described above according to embodiments of the present invention, the light irradiation unit irradiates the measurement part by scanning the light beam 2-dimensionally. Therefore, it is possible to curb deterioration in measurement precision due to an increase in a temperature at the time of measurement of glucose in a human body according to a photoacoustic method.

The present invention is not limited to the above-described embodiment and it is apparent to those skilled in the art that many modifications and combinations can be made within the technical spirit of the present invention.

REFERENCE SIGNS LIST

101 Light irradiation unit
102 Detection unit
103 Light source unit
104 Scanning unit
121 Light beam
151 Measurement part.

The invention claimed is:

1. A component concentration measurement device comprising:
   a light irradiator configured to irradiate a measurement part with a light beam, the light beam having a wavelength absorbed by glucose, wherein the light irradiator irradiates the measurement part by scanning the light beam 2-dimensionally, wherein the light irradiator moves the light beam to a new location of the measurement part from each location of the measurement part before the light beam increases a temperature of tissues of the measurement part; and
   a detector configured to detect a photoacoustic signal generated from the measurement part in response to being irradiated with the light beam.

2. The component concentration measurement device according to claim 1, wherein the light irradiator irradiates the measurement part by performing raster scanning with the light beam.

3. The component concentration measurement device according to claim 1, wherein the light irradiator scans the light beam within a detection range of the detector and irradiates the measurement part.

4. The component concentration measurement device according claim 1, wherein the light irradiator intermittently scans the light beam at a set time interval.

5. The component concentration measurement device according to claim 1, wherein the light irradiator includes:
   a light source configured to generate the light beam; and
   a scanner configured to scan the light beam generated by the light source.

6. The component concentration measurement device according to claim 5, further comprising: a beam shaper configured to extract a central portion of the light beam generated by the light source.

7. The component concentration measurement device according to claim 1, wherein the light irradiator moves the light beam at a scanning speed of 100 μm/10 ms.

8. A method comprising:
   irradiating, by a light irradiator, a measurement part with a light beam, the light beam having a wavelength absorbed by glucose, wherein irradiating the measurement part comprises scanning the light beam 2-dimensionally, wherein the light irradiator moves the light beam to a new location of the measurement part from each location of the measurement part before the light beam increases a temperature of tissues of the measurement part; and
   detecting, by a detector, a photoacoustic signal generated from the measurement part in response to being irradiated with the light beam.

9. The method according to claim 8, wherein irradiating the measurement part comprises performing raster scanning of the measurement part with the light beam.

10. The method according to claim 8, wherein the light irradiator scans the light beam within a detection range of the detector and irradiates the measurement part.

11. The method according to claim 8, wherein the light irradiator intermittently scans the light beam at a set time interval.

12. The method according to claim 8, wherein the light irradiator includes:
    a light source configured to generate the light beam; and
    a scanner configured to scan the light beam generated by the light source.

13. The method according to claim 12, further comprising:
    extracting, by a beam shaper, a central portion of the light beam generated by the light source.

14. The method according to claim 8, wherein the light irradiator moves the light beam at a scanning speed of 100 μm/10 ms.

* * * * *